United States Patent [19]

Izumi et al.

[11] Patent Number: 5,395,822
[45] Date of Patent: Mar. 7, 1995

[54] USE OF PYRUVATE TO PREVENT NEURONAL DEGENERATION ASSOCIATED WITH ISCHEMIA

[76] Inventors: Yukitoshi Izumi, 8912 Eager Rd., Brentwood, Mo. 63144; John W. Olney, 1 Lorenzo La., Ladue, Mo. 63124

[21] Appl. No.: 124,348

[22] Filed: Sep. 20, 1993

[51] Int. Cl.⁶ .................... A61K 37/26; A61K 31/19
[52] U.S. Cl. ......................................... 514/3; 514/557
[58] Field of Search ................................ 514/557, 3

[56] References Cited

U.S. PATENT DOCUMENTS

| | | | |
|---|---|---|---|
| 5,045,454 | 9/1991 | Bertheussen | 435/29 |
| 5,192,762 | 3/1993 | Gray et al. | 514/249 |
| 5,210,098 | 5/1993 | Nath | 514/577 |

OTHER PUBLICATIONS

Remington's Pharmaceutical Sciences (16th Edition) 1980 pp. 1468–1471 and 1490–1493.

*Primary Examiner*—Raymond J. Henley, III
*Attorney, Agent, or Firm*—Patrick D. Kelly

[57] ABSTRACT

This invention discloses a method of using a salt of pyruvic acid (such as sodium pyruvate) to protect against neuronal degeneration due to ischemia (inadequate blood flow, which can be caused by stroke, cardiac arrest, or other events) or due to hypoxia, hypoglycemia, or cellular disorders which interfere with the energy metabolism of neurons. Treatment with pyruvate can be effective even when administered after the onset of an event that triggers neurodegeneration. A preferred mode of use involves co-administration of a pyruvate salt along with one or more agents that block NMDA and/or non-NMDA receptors, or with insulin or a thrombolytic agent.

12 Claims, No Drawings

USE OF PYRUVATE TO PREVENT NEURONAL DEGENERATION ASSOCIATED WITH ISCHEMIA

BACKGROUND OF THE INVENTION

The invention is in the fields of neurology and pharmacology and relates to protecting the brain and central nervous system against damage due to ischemia and other neurological disorders in which energy-providing substrates (oxygen and glucose) are reduced or energy metabolism is suppressed or defective.

The central nervous system (CNS) is comprised of the spinal cord, brain and retina, and contains trillions of nerve cells (neurons) that form networks capable of performing exceedingly complex functions. CNS neurons require energy to survive and perform their physiological functions, and it is generally recognized that the only source of energy for CNS neurons is the glucose and oxygen delivered by the blood (Siesjo 1976). If the blood supply to all or any portion of the CNS is shut off, thereby depriving neurons of both oxygen and glucose (a condition known as ischemia), the deprived neurons rapidly degenerate. This condition of inadequate blood flow is commonly known in clinical neurology as a "stroke." If only the oxygen supply to the brain is interrupted, for example in asphyxia, suffocation or drowning, the condition is referred to as "hypoxia". If only the glucose supply is disrupted, for example when a diabetic takes too much insulin, the condition is called "hypoglycemia". All of these conditions involve energy deficiency and are recognized in clinical medicine as potential causes of brain damage. In the following text, the terms "energy deficiency" or "ischemia" are used interchangeably to refer to any of these conditions that entail CNS energy impairment.

In recent years, neuroscientists have made considerable progress in understanding the mechanism by which energy deficiency leads to neuronal degeneration (for two reviews, see Olney 1989 and Choi 1992). It has been learned that glutamate, which functions under normal and healthy conditions as an important excitatory neurotransmitter in the CNS, can exert neurotoxic properties referred to as "excitotoxicity" if ischemic conditions arise. Normally, glutamate is confined intracellularly, and is only released from a nerve cell at a synaptic junction in tiny amounts, for purposes of contacting a glutamate receptor on an adjacent neuron; this transmits a nerve signal to the receptor-bearing cell. Under healthy conditions, the glutamate released into the extracellular fluid in a synaptic junction is transported back inside a neuron within a few milliseconds, by a highly efficient transport process.

The excitotoxic potential of glutamate is held in check as long as the transport process is functioning properly. However, this transport process is energy dependent (Benveniste et al., 1984), so under ischemic conditions (energy deficiency), glutamate transport becomes incompetent, and glutamate molecules which have been released for transmitter purposes accumulate in the extracellular synaptic fluid. This brings glutamate continually in contact with its excitatory receptors, causing these receptors to be excessively stimulated, a situation which can literally cause neurons to be excited to death. Two additional factors complicate and make matters worse: (1) overstimulated neurons begin to release excessive quantities of glutamate at additional synaptic junctions; this causes even more neurons to become overstimulated, drawing them into a neurotoxic cascade that reaches beyond the initial zone of ischemia; and, (2) overstimulated neurons begin utilizing any available supplies of glucose or oxygen even faster than normal, which leads to accelerated depletion of these limited energy resources and further impairment of the glutamate transport process. Thus, energy deficiency conditions such as stroke, cardiac arrest, asphyxia, hypoxia or hypoglycemia cause brain damage by a compound mechanism; the initial causative mechanism is the ischemia itself, but this leads to failure of the glutamate transport system and a cascade of glutamate-mediated excitotoxic events that are largely responsible for the ensuing brain damage.

In addition to the conditions already mentioned, it has recently become recognized that various defects in the neuron's ability to utilize energy substates (glucose and oxygen) to maintain its energy levels can also trigger an excitotoxic process leading to death of neurons. It has been postulated that this is the mechanism by which neuronal degeneration occurs in neurological diseases such as Alzheimer's dementia, parkinsonism, Huntington's Chorea and amyotrophic lateral sclerosis. For example, evidence for defective intracellular energy metabolism has been found in samples of tissue removed by biopsy from the brains of patients with Alzheimer's disease and this has been proposed as the causative mechanism that triggers an unleashing of the excitotoxic potential of glutamate with death of neurons in Alzheimer's disease thereby being explained by an energy-linked excitotoxic process. Evidence for an intrinsic defect in intracellular energy metabolism has also been reported in parkinsonism and Huntington's Chorea. Thus, rational therapeutic strategies for preventing neuronal degeneration in these disorders would include methods that correct energy deficiency or that prevent excitotoxic neuronal degeneration. This topic was recently reviewed by Beal et al. (1993).

Significant advances have been made in developing methods for preventing or reducing the neuronal damage associated with CNS ischemia. The most active research in this area involves methods of inhibiting excitatory activity at glutamate receptors, using receptor-specific antagonist drugs (in pharmaceutical terminology, a drug that occupies and blocks a certain receptor on a cell surface without triggering activity at that receptor is called an antagonist of that receptor). The glutamate receptors that can mediate excitotoxic neuronal degeneration are broadly divided in two broad categories designated as "NMDA" and "non-NMDA" receptors. NMDA receptors are named after N-methyl-D-aspartate, a drug which does not naturally occur inside the brain, but which was discovered to bind strongly to certain glutamate receptors, which were therefore called "NMDA receptors." The "non-NMDA" class of glutamate receptors has more recently been subdivided into two distinct categories, referred to as KA (kainic acid) receptors and AMPA receptors (formerly called QUIS receptors).

It has been demonstrated repeatedly that NMDA receptor antagonists can protect against CNS ischemic neuronal degeneration in both in vitro tests and a number of in vivo animal models (reviewed by Olney 1989 and Choi 1992); however, various items of more recent evidence suggest that NMDA antagonists may be ineffective in one major type of ischemia known as "global ischemia" and provide only partial protection in the other major type of ischemia, known as "focal" ischemia. Moreover, it appears that NMDA antagonists must be administered immediately at the onset of ischemia to provide significant protection. Experimental evidence pertaining to non-NMDA antagonists is more limited, but the few in vivo animal studies available suggest that these agents may provide significant protection against ischemic neuronal degeneration, even when applied after the ischemic event (Sheardown et al., 1990; LePeillet et al., 1992)

Despite claims that either NMDA or non-NMDA antagonists, used alone, can provide substantial protection against CNS ischemia, a growing body of evidence suggests that the degree of protection afforded by either NMDA or non-NMDA antagonists, alone, is relatively modest. The Applicants have shown (Mosinger et al 1991), and others have recently confirmed (Moroni et al 1993), that a greater degree of protection can be achieved by drugs (or combinations of drugs) that block both NMDA and non-NMDA receptors. For example, protection against ischemic neurodegeneration in the rat retina, in an in vivo test involving actual ischemia in adult mammalian CNS tissue, was in the range of 35 to 40% when either NMDA or non-NMDA antagonists were applied by themselves. This limited degree of protection increased to 80 to 90% protection when a combination of NMDA and non-NMDA antagonists was used. In this ischemia model, protection was defined as delaying the onset of the degenerative process for the duration of the experiment, which was one hour.

A significant limitation of glutamate receptor antagonists as neuroprotectants against ischemic neurodegeneration is that they only insulate the neuron temporarily against degeneration; they do not do anything to correct the energy deficit, or to correct other derangements that occur secondary to the energy deficit. Therefore, although these agents do provide some level of protection against ischemic neurodegeneration in experimental animal models, the protection is only partial and in some cases may only be a delay in the time of onset of degeneration, as mentioned above. However, it is important to note that a delay in the onset of degeneration may be extremely valuable, if there are other drugs or procedures that can be applied during the delay interval to provide additional and/or lasting protection.

One critical factor which is not adequately addressed in most ischemia research concerns the timing of drug administration in relation to the injurious (ischemic) event. This is an important consideration; although some ischemic events can be predicted (for example, involving open-heart surgery), the great majority cannot, and in most cases, therapy can only be initiated during or after an ischemic event. Since CNS cells begin to degenerate very rapidly after the onset of ischemia, there is clearly a need for new neuroprotective methods that are effective when applied after CNS neurons have begun to degenerate.

Another important consideration is whether the ischemia is only transient (e.g. during an episode of cardiac arrest) or is permanent (e.g. following thrombotic or embolic occlusion of CNS blood vessels). If the ischemia is transient, the blood supply carrying oxygen and glucose to the CNS is restored immediately after the event and drugs that prevent neuronal degeneration or promote recovery from the ischemic insult can reach the ischemic tissue through the blood circulation.

If the blood supply to a region of the brain is permanently blocked by a clot, it is not possible by current methods to prevent neuronal degeneration in the center of the ischemic area, because the ischemic tissue is permanently deprived of oxygen and glucose and drugs cannot be delivered to the ischemic tissue through the blocked blood vessel. However, there is a large tissue zone, known as the penumbra, at the circumferential margin of the ischemic area which receives blood from adjoining CNS regions, and this tissue zone is a potential target for drug therapy. Also, drugs that dissolve blood clots (thrombolytic agents, such as streptokinase and tissue plasminogen activator), which currently are being used to treat heart attack victims, are being tested and developed for restoring blood supply to the CNS after a stroke. When such drugs become widely available for CNS use in humans, it will be possible to use them to open the blood vessel so that the ischemic CNS tissue can receive not only oxygen and glucose but also the drugs disclosed herein which can prevent neuronal degeneration or promote recovery from the ischemic insult.

Finally, there are special situations such as thrombotic occlusion of the major artery supplying blood to the retina of the eye, which can be aided by the drugs disclosed herein. When this blood vessel is occluded, it is possible to deliver the drugs of this invention to the ischemic retina by injecting the drug directly into the vitreous of the eye (i.e., into the clear fluid inside the eyeball). The drug can rapidly diffuse from the vitreous into the retina.

SUMMARY OF THE INVENTION

This invention discloses a method of using a salt of pyruvic acid (such as sodium pyruvate) to protect against ischemic neuronal degeneration. This treatment is effective even when administered after an ischemic event. A preferred mode of use involves co-administration of a pyruvate salt along with one or more agents that block NMDA and/or non-NMDA receptors, or with insulin or a thrombolytic agent.

DESCRIPTION OF THE PREFERRED EMBODIMENTS

This invention discloses a method of using pyruvate to protect against ischemic neuronal degeneration. Pyruvate is the ionized form of pyruvic acid ($CH_3COCOOH$). At physiologic pH, the hydrogen proton dissociates from the carboxylic acid group, thereby generating the pyruvate anion ($CH_3COCOO^{--}$). When used as a pharmaceutical, this anion is usually formulated as a salt, using a monovalent or divalent cation such as sodium, potassium, magnesium, or calcium.

Pyruvate is continuously manufactured in the living organism, including the CNS, from glucose. The process by which glucose is converted to pyruvate involves a series of enzymatic reactions that occur anaerobically (in the absence of oxygen). This process is called "glycolysis". A small amount of energy is generated in the glycolytic conversion of glucose to pyruvate, but a much larger amount of energy is generated in a subsequent more complicated series of reactions in which pyruvate is broken down to carbon dioxide and water. This process, which does require oxygen and is referred to as "oxidative respiration", involves the stepwise metabolic breakdown of pyruvate by various enzymes of the Krebs tricarboxylic acid cycle and conversion of the products into high energy molecules by electron transport chain reactions.

Thus, there are two major components to the process by which cells utilize glucose and oxygen to produce energy. The first component entails anaerobic conversion of glucose to pyruvate which releases a small amount of energy, and the second entails oxidative conversion of pyruvate to carbon dioxide and water with the release of a large amount of energy (these metabolic processes have been described in detail in biochemical texts, e.g., Lehninger 1975, pp. 417–441; Stryer 1981, pp. 254–279). For an extensive review of energy metabolism in the brain, see Seisjo, 1978.

Under ischemic conditions, the small amounts of residual glucose and oxygen in the tissues are used up rapidly, within a minute or so, and then neurons become energy deficient, the glutamate transport process fails, and the excitotoxic cascade ensues. Years ago, researchers studying cerebral ischemia in experimental animals reasoned that it might be possible to fortify the CNS against ischemic degeneration by administration of a large amount of glucose prior to the ischemic event. Theoretically, since the glycolytic conversion of glucose to pyruvate can occur in the absence of oxygen and this process can yield a small amount of energy, it should be beneficial. However, it was observed in numerous studies that pre-ischemic administration of glucose caused a marked increase in the severity of brain damage. It is known from numerous other studies that when glucose is available to CNS tissue in the absence of oxygen, the glucose is first converted to pyruvate and then, because oxidative metabolism of pyruvate cannot occur in the absence of oxygen, pyruvate is converted anaerobically to lactate. It is also known that when lactate accumulates in tissues, this causes a lowering of pH (increased acidity) which is referred to as lactic acidosis.

Based on these various observations, early researchers concluded that pre-ischemic administration of glucose is detrimental because it causes lactic acidosis which they postulated might actually be either a primary cause or at least an important contributory factor in the brain damage. This point of view has become very widely accepted among prominent researchers in the ischemia field and is the prevailing position accepted by leading authorities in the field today (e.g., see LeBlanc et al., 1993; Folbergrova et al., 1992; Ginsberg and Busto, 1989).

It logically follows from the above that if glucose is detrimental in cerebral ischemia because it is converted via pyruvate to lactate, then pyruvate would be detrimental as well. In fact, pyruvate might be even more detrimental because the direct conversion of pyruvate to lactate does not entail generation of energy whereas conversion of glucose to pyruvate does entail generation of a small amount of energy. It appears from the literature that researchers in the ischemia field have been so fixated on this point of view over the years and up to the present time that they have never considered, much less tested, the possibility that pyruvate might be beneficial and might even protect neurons against ischemic degeneration. Thus, although the ischemia literature contains many entries pertaining to the measurement of energy metabolites, including pyruvate, the Applicants have not found any reports describing an effort to evaluate pyruvate as a neuroprotectant against ischemic neuronal degeneration.

However, using a hippocampal slice preparation, the Applicants unexpectedly discovered that adding pyruvate after an ischemic episode prevents hippocampal neurons from degenerating, whereas adding glucose after an ischemic event does not prevent such degeneration.

In these experiments, both oxygen and glucose were absent during the ischemic event (20 min). The tissue was then incubated for an additional 90 min in medium that was oxygenated and which contained either glucose or pyruvate. The neurons degenerated in the presence of glucose, but not in the presence of pyruvate.

The most logical explanation for these findings is that the ischemic episode poisons or otherwise blocks, inactivates, or suppresses one or more of the enzymes involved in glycolysis, so that even if glucose becomes available to the CNS during a post-ischemic period, it is not beneficial, because it cannot be converted to pyruvate and used as an energy source. However, pyruvate is protective; it permits CNS neurons to recover from ischemia, by serving as an immediate source of energy if oxygen is also present to permit oxidative release of pyruvate's energy supply. This result indicates that the glycolytic enzyme(s) that are inactivated during ischemia are "upstream" of the pyruvate intermediate; they are somewhere in the pathway leading from glucose to pyruvate. By contrast, the "downstream" enzymes, which control the oxidation of pyruvate once pyruvate has been formed, apparently are not adversely affected by the ischemic event.

As noted above, if glucose is administered to an animal just prior to the onset of cerebral ischemia, this has the paradoxical effect of making the brain damage and neurological outcome much worse. Several studies over the years have shown a related paradox, that if blood glucose is lowered prior to ischemia (by administering insulin), this has a neuroprotective effect. These studies have been interpreted as signifying that the blood glucose level per se is the critical factor (a high blood glucose level being conducive to increased brain damage, and a low blood glucose level being conducive to decreased brain damage). However, a recent report (Voll and Auer 1991), which has not yet provoked a noticeable response in the field of ischemia research, suggests that if insulin is administered along with glucose, the increase in brain damage due to excessive glucose can be avoided and, in fact, the glucose then becomes beneficial. In this situation, the insulin prevented blood glucose levels from becoming abnormally high, but the insulin did not cause blood glucose levels to be lower than normal. Therefore, the beneficial outcome correlates not with a low blood sugar, but with the fact that insulin had been administered. This suggests that insulin may be a useful agent for coadministration with pyruvate.

In addition, the results of the insulin studies raise questions concerning the presumed damaging role of lactic acidosis in brain tissue under ischemic conditions. It is not clear by what mechanism insulin works to make glucose beneficial instead of detrimental in ischemia, but insulin is thought to have many distinct effects, including promotion of glucose entry into the brain from the blood, promotion of uptake of glucose by brain cells, and enhancement of the efficiency of certain enzymes in the glycolytic pathway. Thus, in theory one might explain the beneficial action of insulin in terms of promoting the glycolytic conversion of glucose to pyruvate so that from the beginning of ischemia a small but important amount of energy was being generated for the protection of CNS neurons. However, any extra glucose that was converted anaerobically to pyruvate would have been further converted anaerobically to lactate, and this signifies that an increased accumulation of lactate, contrary to authoritative opinion, may not cause or aggravate ischemic brain damage.

Co-Administration of Glutamate Antagonists and Pyruvate

In an alternate preferred mode of this invention, a pyruvate salt is co-administered with a glutamate receptor antagonist which can penetrate blood-brain barriers. The preferred glutamate antagonist can be any of the following: (1) a selective NMDA antagonist; (2) a selective non-NMDA antagonist, which may suppress activity at KA receptors, or at AMPA receptors, or at both classes of non-NMDA receptors; (3) a mixture of both an NMDA antagonist and a non-NMDA antagonist; (4) a broad-spectrum glutamate receptor antagonist, which significantly inhibits NMDA receptor activity as well as activity as KA and/or AMPA receptors.

Based on preliminary experimental data and on the Applicant's understanding of how these agents interact with neurons under ischemic conditions, it appears likely that pyruvate will provide neuroprotection by a mechanism that is different from, yet complementary to, the mechanism by which glutamate antagonists provide neuroprotection. In brief, glutamate antagonists exert a neuroprotective effect resulting in a delay in onset of neuronal degeneration, whereas pyruvate restores energy, thereby either preventing or arresting the degenerative process and promoting neuronal recovery.

In ischemic or energy-deprived conditions in which oxygen delivery to the brain has been completely stopped, it would be particularly important to administer the glutamate antagonists as early as possible so that they can delay onset of neuronal degeneration. In theory, since pyruvate cannot be utilized for energy if oxygen is totally absent, it might not be of critical importance to administer the pyruvate until the moment that oxygen is returned to the CNS. By waiting until oxygen is restored one would be able to minimize the amount of lactate that would accumulate during the ischemic episode. However, in view of the implications of the Voll and Auer (1991) study suggesting that lactic acidosis is not detrimental provided insulin is available, it might be preferrable under many circumstances to administer pyruvate, together with insulin, as early as possible. In fact, since in most cases the ischemic victim will not come to medical attention until some time after onset of ischemia, as a practical matter it may be necessary in such cases to administer all components of the neuroprotective regimen as early as possible and in a concurrent manner either as separate agents or as a mixture. An additional basis for considering administration of the pyruvate as early as possible is that in many ischemic or energy deficient conditions, the oxygen supply is only partially disrupted, in which case at least some of the administered pyruvate could be utilized for energy throughout the ischemic period.

Co-Administration of Insulin and Pyruvate

As indicated above, it might be advantageous as early as possible in an ischemic situation to administer insulin together with pyruvate. Insulin would appear to permit the residual tissue stores of glucose and perhaps glycogen (although only small amounts of glycogen are present in the brain) to be converted glycolytically from glucose to pyruvate, thereby releasing a small but potentially very important amount of energy during the ischemic episode. Although the pyruvate formed in this process plus any pyruvate administered together with the insulin, in the total absence of oxygen, would be converted to lactate which would contribute to lactic acidosis, lactic acidosis may not be detrimental, as discussed above. Moreover, the amount of lactic acidosis could be minimized by administering only a small amount of pyruvate in the initial combination therapy and a larger amount later, when oxygen is returned to the brain. By administering a small amount of pyruvate early, one would assure that the brain would have pyruvate available in situ for immediate use the moment oxygen is restored.

Co-Administration of Safening Agents

If desired, an additional drug (referred to herein as a "safening agent") can also be co-administered, if an NMDA antagonist is used, to reduce certain adverse side effects of the NMDA antagonist. Research by one of the Applicants some years ago revealed that NMDA antagonists can damage or kill certain types of neurons in the cingulate/retrosplenial cortex (Olney et al 1989). Subsequently, the Applicant identified two types of safening agents which can avoid the toxic side effects while still allowing NMDA antagonists to exert their primary protective activity. These two classes of agents are (1) certain anti-cholinergic drugs, such as scopolamine (see U.S. Pat. No. 5,034,400, Olney, 1991); (2) barbiturates such as secobarbital, pentobarbital, and thiamylal, which act as so-called "direct agonists" of gamma-amino-butyric acid (GABA) receptors (see Olney et al 1991).

Co-Administration of Thrombolytic Agents

Another class of drugs called thrombolytic agents can also be co-administered with pyruvate. As suggested by their name, thrombolytic agents (such as streptokinase or tissue plasminogen activator) can break apart ("lyse") blood clots ("thromboses"). If a formulation containing a thrombolytic agent is injected into the blood of a person having a stroke, the thrombolytic agent, if it can reach the blood clot which is causing the problem, can help dissolve it and restore blood flow through the blocked artery. If the injected formulation also contains a pyruvate salt, the pyruvate will be delivered to the ischemic zone immediately, where it can provide an energy source to the cells, as soon as the blood clot is dissolved.

Simultaneous or Sequential Administration of Pyruvate and Other Agents

As indicated above, in some situations it might be advantageous to administer glutamate antagonists prior to the administration of pyruvate to a patient suffering an ischemic or similar event, for early protection of the neurons during the oxygen-deficient period. However, as indicated above, in most cases it will be advantageous and more practical to administer pyruvate together with other agents, either as a mixture, or simultaneously, or in rapid sequence. To appreciate this point, it is necessary to consider several examples of the major purposes for which this therapy would be indicated:

Cardiac Bypass Surgery

In this situation, one knows ahead of time that damage to the brain might occur due to energy deficiency while the blood circulation is being manipulated for cardiac surgical purposes. In advance it will be advantageous to administer glutamate antagonists plus pyruvate and insulin so that if the brain becomes transiently ischemic these agents will have already been delivered to the brain; the glutamate receptor antagonists can act immediately, insulin can promote the use of residual glucose or glycogen stores for small amounts of immediate energy and pyruvate will remain in situ in the brain ready to be utilized for energy as soon as oxygen is returned to the tissue. The pyruvate will actually be maintained in the brain as lactate but as soon as oxygen becomes available the lactate is converted back to pyruvate. Or, if the ischemia is only partial so that some oxygen is still being delivered to the brain, pyruvate will be advantageous from the onset of the ischemic event.

Cardiac Arrest

In this condition the blood to the CNS is suddenly shut off but it will be restored as soon as the heart begins beating again or as soon as resuscitative measures are initiated. Since there is no warning that the ischemic episode might occur, there is no opportunity to administer agents in advance. However, immediately at the onset of resuscitation a combination of glutamate antagonists plus pyruvate should be given so that the glutamate antagonists can protect against neurodegeneration during the few minutes that are required for pyruvate plus oxygen to achieve restoration of energy levels to normal. It seems likely that simultaneous administration of insulin would also be beneficial in this situation and there is no basis for believing that insulin in small doses would be disadvantageous or detrimental.

Cerebral thrombosis or embolism

In this condition, the blood to a portion of the brain is suddenly shut off by a clot or embolis lodging in the blood vessel serving that brain region. This occurs without warning so therapy cannot commence until after onset of the ischemic episode. Again, it will be advantageous to administer a combination of glutamate antagonist plus pyruvate as soon as the patient presents to the emergency room. The therapeutic target initially will be the penumbra zone at the circumferential margin of the ischemic tissue. In this region energy deficiency is severe enough to cause neurons to slowly degenerate but blood circulation to adjoining brain regions can allow small amounts of neuroprotective accents and oxygen to get to the ischemic tissue by diffusion. Therefore, administering a combination of glutamate antagonists plus pyruvate intravenously will provide for the glutamate antagonists to begin protecting neurons against degeneration while the pyruvate plus oxygen diffuse into the ischemic penumbral zone and restore energy levels. Time is of the essence, so even if it is only a few minutes of protection provided by the glutamate antagonists before pyruvate and oxygen can restore energy levels, this could make the difference between death and survival of thousands or millions of neurons. Again, it seems likely that simultaneous administration of small doses of insulin would also be beneficial in this situation and there is no basis for believing that it would be disadvantageous or detrimental.

In the near future, when clot dissolving agents are available for application in cerebral thrombosis patients, it will be advantageous to administer as early as possible a combination of glutamate antagonists plus pyruvate and insulin so that they can begin working in a complementary manner as soon as the clot is dissolved and these drugs plus oxygen can be delivered to the ischemic tissue.

Central Retinal Artery Occlusion

In this condition, blood is shut off to the retina and retinal degeneration typically occurs relatively rapidly if energy is not restored. It is possible to administer glutamate antagonists into the vitreous (the watery liquid inside the eye ball) and they will diffuse directly into the ischemic retinal tissue to protect neurons against degeneration. We have shown that glutamate antagonists prevent onset of degeneration in the ischemic retina for up to 1 hour after intravitreal administration. However, administration of pyruvate will be beneficial only to the extent that a supply of oxygen is available to the tissue. In many cases, when the blood supply to the eye is blocked, it is only a partial blockade, in which case the retina might still be receiving enough oxygen to allow the pyruvate to be used for energy. Alternatively, after introducing the pyruvate into the vitreous, it may be feasible to deliver oxygen to the retina by placing a hyperbaric chamber (in the form of airtight rigid goggles) over the eyes and filling the chamber with oxygen under increased pressure. In either case it would be advantageous as soon as the ischemic event is diagnosed to administer intravitreally a combination of glutamate antagonist and pyruvate. Administering them as a single compound formulation would be advantageous in that making multiple separate injections of different agents into the vitreous would increase risk of physical damage to the eye.

Salts and Formulations

Since pyruvate dissociates at neutral pH to form an anion, $CH_3COCOO^{--}$, it can be formulated for pharmaceutical use as a salt using a monovalent cation (such as sodium or potassium pyruvate) or a divalent cation (such as calcium or magnesium pyruvate). Any pharmacologically acceptable salt can be used, provided that it is suitable and practical for administration to humans, sufficiently stable under reasonable storage conditions to have an adequate shelf life, and physiologically acceptable when introduced into the body by a suitable route of administration. The nature of the salt is not critical, provided that it is non-toxic and does not substantially interfere with the desired activity.

It is anticipated that in a number of preferred embodiments, this invention will be used mainly to reduce neuronal damage in acute crises (such as during or after a stroke or cardiac arrest, or after a drowning or suffocation event), or in conjunction with major surgery such as cardiac surgery. Accordingly, the main route of initial administration will involve hypodermic injection or intravenous infusion. If blood flow to a major portion of the brain has been cut off, it is also possible, by drilling through the skull, to inject a treatment compound directly into a brain ventricle which normally contains cerebrospinal fluid (see, e.g., U.S. Pat. No. 4,446,155, Osterholm 1984). Administration of pyruvate by these methods for acute treatment could be followed by oral administration if desired, which would last until the patient has sufficiently recovered from the crisis. In addition, if it is determined by further research that neuronal degeneration in chronic neurodegenerative diseases such as Alzheimer's, Huntington's or Parkinson's diseases is caused by an impairment in intracellular energy metabolism, especially if the impairment were in the glycolytic pathway, pyruvate could be administered orally on a chronic basis to maintain energy in CNS neurons at a level that will protect the neuron from degenerating. Typical dosages of pyruvate, which will depend on factors such as the size and condition of the patient and the amount of time that has elapsed since the onset of a stroke before treatment begins, would be in the range of about 10 to about 100 gm/day for an adult for intravenous injection or infusion, and about 25 to about 150 gm/day for oral administration.

If desired, pyruvate can be injected into the bloodstream using both rapid-release and sustained-release techniques, to sustain a relatively stable elevated pyruvate concentration in the circulating blood over a period such as 12 or 24 hours. Since pyruvate is highly water-soluble, a rapid-release bolus does not need to be specially formulated; it can simply be injected or infused intravenously in an aqueous carrier such as buffered saline. An additional slow-release component can be provided by any of several means, such as through the use of (1) an infusion pump which is coupled to a blood vessel via a catheter, or (2) subcutaneous implantation of a salt of pyruvate contained in a slowly dissolving biodegradable matrix.

This invention also discloses three articles of manufacture which will help facilitate the rapid and effective use of this invention to minimize brain damage. The first article of manufacture comprises a single dosage of a suitable pyruvate salt (which can also contain insulin and/or a glutamate antagonist, as discussed above, if desired) pre-loaded into a sterile hypodermic syringe, at a dosage which can be safely administered to an apparent stroke victim before a complete diagnosis of the patient has been made (i.e., this dosage will help reduce brain damage in a victim of stroke, drowning, or suffocation, but it will not inflict significant damage on the patient if it turns out that the problem which felled the patient was not an ischemic event such as a stroke). This pre-loaded hypodermic dosage could be administered by ambulance or emergency room attendants or nurses who have been trained to recognize the symptoms of stroke, for use during the critical carry-over period until the patient can receive intensive care from a doctor. This pre-loaded hypodermic syringe could contain a dosage of about 2 to about 10 gm of pyruvate.

The second article of manufacture comprises a sterile sealed bottle which can be used to fill a hypodermic syringe, filled with a suitable dosage (such as about 2 to about 10 gm) of a pyruvate salt. Such bottles typically contain a watertight sealing plug made of rubber or a soft plastic that can be easily penetrated by a hypodermic needle. As with a pre-filled syringe, the bottle can also contain insulin and/or a glutamate antagonist if desired. A typical 250 ml infusion bag can contain a suitable aqueous carrier containing about 10 to about 50 gm/l of the pyruvate salt.

The second article of manufacture comprises a sterile sealed intravenous infusion bag filled with a suitable pyruvate salt. The infusion bag can also contain insulin and/or a glutamate antagonist if desired. A typical 250 ml infusion bag can contain a suitable aqueous carrier containing about 10 to about 50 gm/l of the pyruvate salt.

EXAMPLES

Example 1

Protection against ischemic neurodegeneration by blocking both NMDA and non-NMDA glutamate receptors from the onset of ischemia The Applicants have conducted studies using an in vivo retina ischemia model in which the adult rat retina is rendered ischemic by causing blood clots to form in the major blood vessels supplying blood to the eye (Mosinger and Olney, 1989). Briefly, this is carried out by injecting a photoreactive dye (rose bengal) into the tail vein of a rat. After the dye has circulated throughout the blood stream, the rat is anesthetized and its eyes exposed to a bright light, which causes dye molecules in the retinal blood vessels to react in a manner that causes clot formation and occlusion of retinal blood vessels, thereby rendering the retina ischemic. In these experiments, both eyes are subjected to ischemia and one eye of an animal serves as a control, while the other eye is experimentally treated with a neuroprotective agent such as a glutamate antagonist.

Within an hour after onset of vascular occlusion, the unprotected (control) retina shows severe signs of neurodegeneration. If glutamate receptor antagonists are injected into the vitreous of the other eye at the beginning of the experiment, just before occluding the blood supply, they confer significant protection against ischemic neuronal degeneration. If MK-801, an NMDA glutamate receptor antagonist is injected into the vitreous, a protection level which usually averages about 40% is achieved. If CNQX, a non-NMDA glutamate receptor antagonist, is injected into the vitreous, the protection is approximately 35%. If a combination of MK-801 plus CNQX is injected into the vitreous, the protection can be increased to approximately 80%.

The same principle can be demonstrated by using kynurenic acid, an antagonist that simultaneously blocks both NMDA and non-NMDA receptors. This agent provides roughly 90% protection.

Thus, by blocking either NMDA or non-NMDA glutamate receptors, partial protection against retinal ischemic damage can be obtained, while if both types of receptors are blocked, almost complete protection is achieved.

It should be mentioned that in this model, "protection" signifies that onset of the degenerative reaction has been delayed for the duration of the experiment, i.e., for 1 hour.

These results are described in a recent publication (Mosinger et al 1991).

Example 2

Comparison of results in Example 1 with results in the ischemia literature

In the late 1980s several research groups, using a variety of ischemia models, reported that NMDA glutamate receptor antagonists protect the in vivo animal against ischemic brain damage (Simon et al., 1984; Gill et al., 1987; Boast et al., 1987; McDonald et al., 1987; Park et al., 1988; Kochhar et al., 1988; Olney et al., 1989; Swan and Meldrum 1990).

However, subsequently, numerous reports raised questions about the ability of NMDA antagonists to confer such protection (Fleischer et al., 1989; Michenfelder et al., 1989; Buchan and Pulsinelli, 1990; Yao et al., 1993; Lanier et al., 1990, Nellgard et al., 1991; Sterz et al., 1989).

While all of the experimental conditions were not the same in the first and second series of studies, the ability of NMDA antagonists, when administered by themselves, to protect against ischemic neuronal degeneration remains unclear. There is good agreement that they are effective for prevention of ischemic neurodegeneration in the immature CNS (McDonald et al., 1987; Olney et al., 1989), but they may be only variably and partially effective in the adult CNS unless accompanied by a non-NMDA antagonist (Mosinger et al., 1991). Moreover, it appears that they must be administered at the onset of ischemia to be even partially effective in the adult CNS.

Experience in evaluating non-NMDA antagonists has been more limited, because agents which can block non-NMDA receptors and which also can penetrate mammalian blood-brain barriers were not available until 1990. However, the initial reports suggest that non-NMDA antagonists, when administered by themselves either before or after the ischemic insult, may be more effective than NMDA antagonists in protecting the adult mammalian CNS against ischemic neurodegeneration (Sheardown et al., 1990; Le Peillet et al., 1992). However, the amount of protection conferred by non-NMDA antagonists in these studies, although statistically significant, was of a modest degree. There have been no studies published to date that show a high degree of protection from either NMDA or non-NMDA antagonists alone, comparable to the protection reported in Mosinger et al. (1991) which used drugs that simultaneously block both NMDA and non-NMDA receptors. Until very recently, except for the study of Mosinger et al (1991), researchers tended to test either NMDA or non-NMDA antagonists by themselves but did not attempt to evaluate the two classes of drugs in combination. However, very recently the findings of Mosinger et al (1991) were independently confirmed by another group (Moroni et al., 1993) who used a wider selection of NMDA and non-NMDA antagonists, both alone and in combination. The results reported by these authors were essentially identical to those reported early by Mosinger et al (1991).

In summary, available evidence suggests that NMDA antagonists are highly effective in protecting against hypoxic/ischemic brain damage in the immature CNS, that either NMDA or non-NMDA antagonists may be effective in preventing ischemic damage in the adult CNS but the degree of protection is rather limited unless both NMDA and non-NMDA receptors are blocked simultaneously and unless the agents are introduced at the onset of ischemia. Preliminary evidence suggests that non-NMDA antagonists may be more effective than NMDA antagonists when administered after the ischemic event.

Example 3

In vitro hippocampal slice studies showing protection against ischemic neurodegeneration by puruvate Albino rats (30±2 days old, 75-125 g) are deeply anesthetized with halothane and decapitated using a guillotine. The hippocampus is rapidly dissected out and placed in cold (4°-6° C.) artificial cerebrospinal fluid (ACSF) which has been modified by changing the concentration of $MgSO_4$ from 2 to 4 mM and the concentration of $CaCl_2$ from 2 mM to 1 mM. This solution contains 10 mM glucose and is continuously gassed with 95% $O_2$ value to provide oxygen and maintain pH in a neutral range (pH 7.3±0.05). While the tissue is in this solution, transverse slices (typically 500 um thick) are cut using a WPI Vibroslicer. These slices are then transferred to a standard ACSF solution which contains 10 mM glucose and is continuously gassed with 95% $O_2$ and 5% $CO_2$. They are left in this solution for 1 hour at 34° C. to equilibrate before being exposed to ischemic conditions. This protocol routinely produces slices that remain healthy and retain a normal histological appearance for up to 6 hours of incubation in the standard gassed ACSF solution containing glucose. For histological experiments, slices from the same animal are incubated in parallel in individual 10 ml beakers. Each hippocampus provides 6-8 slices. Thus experimental and control operations are performed at the same time on slices prepared from the same animal. All procedures are performed at 34° C.

To induce simulated ischemic conditions, glucose is removed from the standard ACSF medium and the slice is incubated in the glucose-free medium for 20 minutes during which the chamber is free of $O_2$ (the solution is gassed with 95% $N_2$ and 5% $CO_2$). After 20 minutes of ischemia (i.e., $O_2$ and glucose deprivation), the slices are transferred to standard ACSF medium containing either 10 mM glucose or 10 mM pyruvate. They are incubated in these solutions for an additional 90 min, during which the solution is being oxygenated with 95% $O_2$-5% $CO_2$. Thus, the hippocampal slice is preincubated for 1 hour in medium containing glucose and $O_2$, then it is deprived of glucose and $O_2$ for 20 min and then is post-incubated for 90 min in medium containing $O_2$ plus either glucose or pyruvate. At least 6 hippocampal slices are studied for each experimental condition.

After completion of the incubations, slices are fixed in 1% paraformaldehyde and 1.5% glutaraldehyde overnight at 4° C. Slices are then rinsed in 0.1M pyrophosphate buffer, placed in 1% buffered osmium tetroxide for 1 hour, and dehydrated with alcohol and toluene. Slices are then embedded in araldite, cut into 1 um sections, stained with methylene blue and azure II, and evaluated by light microscopy. Damage in the CA1 region of the hippocampus is rated on a scale of 0 (completely intact) to 4 (severe degeneration of pyramidal neurons) by a trained pathologist or histologist. Rating is done blind, using numbered codes to conceal experimental conditions from the analyst.

Using this rating system, control slices that are incubated for two hours in the standard solution (without ischemia) were rated as 0.2±0.1 (n=34). If hippocampal slices were evaluated immediately after the 20 min ischemic event, significant degenerative changes had not occurred (rating 0.3±0.2, n=6), but if exposed to ischemia and then postincubated for 90 min in medium containing glucose and $O_2$, severe degeneration was present (rating 3.7±0.1, n=11). However, exposure to ischemia followed by 90 min postincubation in medium containing pyruvate and $O_2$ resulted in considerable protection against ischemic degeneration (rating 1.2±0.2, n=6). In both of these cases, the tissue was exposed to the same ischemic condition for 20 minutes; the only difference was that pyruvate instead of glucose was present during the 90 min postincubation.

In other experiments, the conditions were varied. For example, in one set of experiments, glucose and $O_2$ were present during the postincubation intervals and pyruvate was present during the 20 min ischemic interval. Histological evaluation of the slice after the postincubation interval revealed that the hippocampal neurons had degenerated severely (rating 3.3±0.4, n=6). Thus, pyruvate protected against degeneration if it was introduced during the postincubation interval when $O_2$ was present, but not if its presence was restricted to the ischemic interval when oxygen was absent.

REFERENCES

Beal, M. F., et al, "Do defects in mitochondrial energy metabolism underlie the pathology of neurodegenerative diseases?" *Trends Neurosci.* 16: 125-131 (1993)

Benveniste, H., et al., "Elevation of the extracellular concentrations of glutamate and aspartate in rat hippocampus during transient cerebral ischemia monitored by intracerebral microdialysis," *J. Neurochem.* 43: 1369-1374 (1984)

Block, G. A. and Pulsinelli, W. "Excitatory amino acid receptor antagonists: Failure to prevent ischemic neuronal damage," *J. Cereb. Blood Flow Metab.* 7 (suppl 1): 149 (1987)

Boast, C. A., et al., "The N-methyl-D-aspartate antagonists CGS 19755 and CPP reduce ischemic brain damage in gerbils," *Brain Res.* 442:345-348 (1987)

Buchan, A., and Pulsinelli, W. A. "Hypothermia but not the N-methyl-D-aspartate antagonist, MK801, attenuates neuronal damage in gerbils subjected to transient global ischemia," *J. Neurosci.* 10:311-316 (1990)

Choi, D. W., "Excitotoxic Cell Death," *J. Neurobiol* 23: 1261-1276. (1992)

Fleischer, E. J., et al., "MK-801, an excitatory amino acid antagonist, does not improve neurologic outcome following cardiac arrest in cats," *J. Cereb. Blood Flow Metab.* 9:795-804 (1989)

Folbergrova, J., et al., "Focal and perifocal changes in tissue energy state during middle cerebral artery occlusion in normo- and hyperglycemic rats," *J. Cereb. Blood Flow Metab.* 12: 25-33 (1992)

Ginsberg, M. D. and Busto, R., "Rodent models of cerebrasl ischemia (Progress Review)," *Stroke* 20:1627-1640 (1989)

Kochhar, A., et al., "Glutamate antagonist therapy reduces neurologic deficits produced by focal central nervous system ischemia," *Arch. Neurol.* 45: 148-153 (1988)

Lanier, W. L., et al., "The effect of dizocillipine maleate (MK-801), an antagonist of N-methyl-D-aspartate receptor, on neurological recovery and histopathology following complete cerebral ischemia in primates," *J. Cereb. Blood Flow Metab.* 10: 252-261 (1990)

LeBlanc, M. H., et al., "Glucose affects the severity of hypoxic-ischemic brain injury in newborn pigs," *Stroke* 24:1055-1062 (1993)

Lehninger, A., *Biochemistry* (Worth Publ., New York, 1975)

LePeillet E., et al., "The non-NMDA antagonists, NBQX and GYKI 52466, protect against cortical and striatal cell loss following transient global ischaemia in the rat," *Brain Res.* 571: 115-120 (1992)

McDonald, J. W., et al., "MK-801 protects the neonatal brain from hypoxic-ischemic damage," *Eur. J. Pharmacol.* 140:359-361 (1987)

Michenfelder, J. D., et al., "Evaluation of the glutamate antagonist dizocilpine (MK-801) on neurologic outcome in a canine model of complete cerebral ischemia: correlation with hippocampal histopathology," *Brain Res.* 481: 228-234 (1989)

Mosinger, J. L. and Olney, J. W., "Photothrombosis-induced ischemic neuronal degeneration in the rat retina," *Exp. Neurol.* 105: 110-113, (1989)

Mosinger, J. L., et al., "Blockade of both NMDA and non-NMDA receptors is required for optimal protection against ischemic neuronal degeneration in the in vivo adult mammalian retina," *Exp. Neurol.* 113:10-17 (1991)

Nellgard, B., et al., "Lack of protection by the N-methyl-D-aspartate receptor blocker dizocilpine (MK-801) after transient severe cerebral ischemia in the rat, "Anesthesiology 75: 279-287 (1991)

Olney, J. W., "Excitatory amino acids and neuropsychiatric disorders," *Biol. Psychiatry* 26:505-525 (1989)

Olney, J. W., et al , "MK-801 prevents hypobaric-ischemic neuronal degeneration in infant rat brain," *J. Neurosci* 9: 1701-1704 (1989a)

Olmey. J. W., "NMDA antagonist neurotoxicity: Mechanism and prevention," *Science* 254: 1515-1518 (1991)

Park, C. K., et al., "Focal cerebral ischaemia in the cat: treatment with the glutamate antagonist MK-801 after induction of ischaemia," *J. Cereb Blood Flow Metab.* 8: 757-762 (1988)

Siesjo, B. K., *Brain Energy Metabolism* (John Wiley & Sons, New York, 1978)

Sheardown, M. J., et al., "2 3-Dihydroxy-6-nitro-7-sulfamoylbenzo(f)quinoxaline: a neuroprotectant for cerebral ischemia," *Science* 247:571-574 (1990)

Simon, R. P., et al., "Blockade of N-methyl-D-aspartate receptors may protect against ischemic damage in the brain," *Science* 226: 850-852 (1984)

Sterz, F., et al., "Effect of excitatory amino acid receptor blocker MK-801 on overall and neurological outcome after prolonged cardiac arrest in dogs," *Anesthesiology* 71:907-918 (1989)

Stryer, L., *Biochemistry* (Freeman Publ., San Francisco, 1981)

Swan, J. H. and Meldrum, B. S., "Protection by NMDA antagonists against selective cell loss following transient ischemia," *J. Cereb. Blood Flow Metab* 10: 343-351 (1990)

Voll, C. L. and Auer, R. N. "Insulin attenuates ischemic brain damage independent of its hypoglycemic effect," *J. Cereb. Blood Flow and Metabolism* 11: 1006-1014 (1991)

Yao, H., et al., "Failure of MK-801 to reduce infarct volume in thrombotic middle cerebral artery occlusion in rats," *Stroke* 24: 864-871 (1993)

We claim:

1. A method of protecting a mammalian central nervous system against neuronal degeneration triggered by an ischemic event, comprising the step of injecting, into the bloodstream of a mammal at risk of ischemic damage, a therapeutically effective quantity of a pharmaceutically acceptable salt of pyruvate, in a manner which provides pyruvate to neurons to promote oxidative metabolism, wherein the salt of pyruvate, calcium pyruvate, potassium pyruvate, and magnesium pyruvate.

2. The method of claim 1 wherein the salt of pyruvate is administered to the mammal in conjunction with a therapeutically effective quantity of at least one glutamate receptor antagonist capable of penetrating a mammalian blood-brain barrier and suppressing excitatory activity in mammalian neurons during ischemia.

3. The method of claim 2 wherein the salt of pyruvate is administered to the mammal in conjunction with a first glutamate receptor antagonist capable of penetrating a mammalian blood-brain barrier and suppressing excitatory activity at NMDA receptors, and a second glutamate receptor antagonist capable of penetrating a mammalian blood-brain barrier and suppressing excitatory activity at non-NMDA receptors.

4. The method of claim 1 wherein the salt of pyruvate is administered to the mammal in conjunction with insulin.

5. The method of claim 1 wherein the salt of pyruvate is administered to the mammal in conjunction with a thrombolytic agent.

6. A method of protecting a mammalian central nervous system against neuronal degeneration caused by hypoxia, comprising the step of injecting, into the bloodstream of a mammal at risk of neuronal degeneration caused by hypoxia, a therapeutically effective quantity of a pharmaceutically acceptable salt of pyruvate, in a manner which provides pyruvate to neurons to promote oxidative metabolism, wherein the salt of pyruvate is selected from the group consisting of sodium pyruvate, calcium pyruvate, potassium pyruvate, and magnesium pyruvate.

7. The method of claim 6 wherein the salt of pyruvate is administered to the mammal in conjunction with a therapeutically effective quantity of at least one glutamate receptor antagonist capable of penetrating a mammalian blood-brain barrier and suppressing excitatory activity in mammalian neurons during a hypoxic event.

8. The method of claim 7 wherein the salt of pyruvate is administered to the mammal in conjunction with a first glutamate receptor antagonist capable of penetrating a mammalian blood-brain barrier and suppressing excitatory activity at NMDA receptors, and a second glutamate receptor antagonist capable of penetrating a mammalian blood-brain barrier and suppressing excitatory activity at non-NMDA receptors.

9. The method of claim 6 wherein the salt of pyruvate is administered to the mammal in conjunction with insulin.

10. The method of claim 6 wherein the salt of pyruvate is administered to the mammal in conjunction with a thrombolytic agent.

11. A composition of matter intended for injection into a mammalian patient, consisting essentially of insulin and a pharmaceutically acceptable salt of pyruvate in an injectable carrier liquid, wherein both the insulin and the salt of pyruvate are present at therapeutically effective concentrations which, if injected into a mammal suffering a stroke, can reduce neuronal damage and necrosis, and wherein the composition of matter is further characterized by the absence of any additional compounds that would diminish the suitability of the composition for injection into a mammalian patient suffering a stroke.

12. A method of protecting a mammalian central nervous system against neuronal degeneration caused by a defect in at least one intracellular energy metabolic enzyme, comprising the step of administering to a mammal at risk of such neuronal degeneration a therapeutically effective quantity of a pharmaceutically acceptable salt of pyruvate, in a manner which provides pyruvate to neurons to promote oxidative metabolism wherein the salt of pyruvate is selected from the group consisting of sodium pyruvate, calcium pyruvate, potassium pyruvate, and magnesium pyruvate.

* * * * *